(12) United States Patent
Korkuch et al.

(10) Patent No.: US 11,045,634 B2
(45) Date of Patent: Jun. 29, 2021

(54) PEEL AWAY HEMOSTASIS VALVE

(71) Applicant: Abiomed, Inc., Danvers, MA (US)

(72) Inventors: Christopher Nason Korkuch, Beverly, MA (US); Glen R. Fantuzzi, Arlington, MA (US)

(73) Assignee: ABIOMED, INC., Danvers, MA (US)

( * ) Notice: Subject to any disclaimer, the term of this patent is extended or adjusted under 35 U.S.C. 154(b) by 114 days.

(21) Appl. No.: 16/182,225

(22) Filed: Nov. 6, 2018

(65) Prior Publication Data

US 2019/0134374 A1 May 9, 2019

Related U.S. Application Data

(60) Provisional application No. 62/582,075, filed on Nov. 6, 2017.

(51) Int. Cl.
*A61M 39/06* (2006.01)
*A61M 25/06* (2006.01)
*A61M 60/135* (2021.01)

(52) U.S. Cl.
CPC ........ *A61M 39/06* (2013.01); *A61M 25/0668* (2013.01); *A61M 39/0606* (2013.01); *A61M 60/135* (2021.01); *A61M 2025/0675* (2013.01); *A61M 2039/064* (2013.01); *A61M 2039/0626* (2013.01)

(58) Field of Classification Search
None
See application file for complete search history.

(56) References Cited

U.S. PATENT DOCUMENTS 4,317,445 A 3/1982 Robinson
4,380,252 A 4/1983 Gray et al.
(Continued)

FOREIGN PATENT DOCUMENTS

CN 104174107 A 12/2014
EP 1212185 A1 6/2002
(Continued)

OTHER PUBLICATIONS

International Search Rerport for International Patent Application No. PCT/US2018/059486, dated Apr. 30, 2019.
(Continued)

*Primary Examiner* — Carl H Layno
*Assistant Examiner* — Manolis Pahakis
(74) *Attorney, Agent, or Firm* — Botos Churchill IP Law LLP

(57) ABSTRACT

A hemostasis valve body provides strong sealing around a medical device during insertion of the medical device into a blood vessel, low forces for tearing, and stability during insertion of the medical devices as well as during peel away. The valve body comprises a first surface, a second surface opposite the first surface, an edge, helical slits, and a pair of longitudinal cuts. The helical slits are positioned at a center of the valve body and traverse the first surface to the second surface. The helical slits provide a seal around the medical device. Each respective longitudinal cut extends from the first surface partially through the valve body to a depth short of the second surface for at least part of a length of the respective longitudinal cut. The longitudinal cuts facilitate a separation of the valve body into two parts during a peel away action.

21 Claims, 11 Drawing Sheets

(56) References Cited

U.S. PATENT DOCUMENTS

| | | | |
|---|---|---|---|
| 4,402,685 A | 9/1983 | Buhler et al. | |
| 4,569,347 A | 2/1986 | Frisbie | |
| 4,651,751 A | 3/1987 | Swendson et al. | |
| 4,699,611 A | 10/1987 | Bowden | |
| 4,798,594 A | 1/1989 | Hillstead | |
| 4,895,346 A * | 1/1990 | Steigerwald | A61M 39/0613 137/849 |
| 4,895,565 A | 1/1990 | Hillstead | |
| 5,041,095 A * | 8/1991 | Littrell | A61M 39/0606 604/167.04 |
| 5,069,674 A | 12/1991 | Fearnot et al. | |
| 5,114,408 A * | 5/1992 | Fleischhaker | A61M 39/0606 604/167.04 |
| 5,139,486 A | 8/1992 | Moss | |
| 5,180,372 A | 1/1993 | Vegoe et al. | |
| 5,221,255 A | 6/1993 | Mahurkar et al. | |
| 5,234,425 A | 8/1993 | Fogarty et al. | |
| 5,279,596 A | 1/1994 | Castaneda et al. | |
| 5,304,142 A | 4/1994 | Liebl et al. | |
| 5,312,355 A | 5/1994 | Lee | |
| 5,320,611 A | 6/1994 | Bonutti et al. | |
| 5,350,363 A * | 9/1994 | Goode | A61M 39/0606 604/167.04 |
| 5,380,304 A | 1/1995 | Parker | |
| 5,395,341 A | 3/1995 | Slater | |
| 5,397,310 A | 3/1995 | Chu et al. | |
| 5,397,311 A | 3/1995 | Walker et al. | |
| 5,405,338 A | 4/1995 | Kranys | |
| 5,407,430 A | 4/1995 | Peters | |
| 5,409,463 A | 4/1995 | Thomas et al. | |
| 5,409,469 A | 4/1995 | Schaerf | |
| 5,488,960 A | 2/1996 | Toner | |
| 5,492,530 A | 2/1996 | Fischell et al. | |
| 5,520,655 A * | 5/1996 | Davila | A61M 39/0606 604/167.04 |
| 5,536,255 A | 7/1996 | Moss | |
| 5,573,517 A | 11/1996 | Bonutti et al. | |
| 5,599,326 A | 2/1997 | Carter | |
| 5,653,697 A | 8/1997 | Quiachon et al. | |
| 5,713,867 A | 2/1998 | Morris | |
| 5,752,937 A | 5/1998 | Otten et al. | |
| 5,795,341 A | 8/1998 | Samson | |
| 5,827,242 A | 10/1998 | Follmer et al. | |
| 5,911,702 A | 6/1999 | Romley et al. | |
| 5,935,122 A | 8/1999 | Fourkas et al. | |
| 5,971,993 A | 10/1999 | Hussein et al. | |
| 6,042,578 A | 3/2000 | Dinh et al. | |
| 6,068,622 A | 5/2000 | Sater et al. | |
| 6,165,163 A | 12/2000 | Chien et al. | |
| 6,197,014 B1 | 3/2001 | Samson et al. | |
| 6,197,016 B1 | 3/2001 | Fourkas et al. | |
| 6,217,565 B1 | 4/2001 | Cohen | |
| 6,258,080 B1 | 7/2001 | Samson | |
| 6,290,692 B1 | 9/2001 | Klima et al. | |
| 6,338,730 B1 | 1/2002 | Bonutti et al. | |
| 6,363,273 B1 | 3/2002 | Mastrorio et al. | |
| 6,379,346 B1 | 4/2002 | McIvor et al. | |
| 6,423,052 B1 | 7/2002 | Escano | |
| 6,428,556 B1 | 8/2002 | Chin | |
| 6,508,966 B1 | 1/2003 | Castro et al. | |
| 6,544,270 B1 | 4/2003 | Zhang | |
| 6,562,049 B1 | 5/2003 | Norlander et al. | |
| 6,589,227 B2 | 7/2003 | Sønderskov Klint | |
| 6,613,038 B2 | 9/2003 | Bonutti et al. | |
| 6,692,462 B2 | 2/2004 | Mackenzie et al. | |
| 6,702,972 B1 | 3/2004 | Markle | |
| 6,740,073 B1 | 5/2004 | Saville | |
| 6,749,600 B1 | 6/2004 | Levy | |
| 6,814,715 B2 | 11/2004 | Bonutti et al. | |
| 6,824,553 B1 | 11/2004 | Samson et al. | |
| 6,827,710 B1 | 12/2004 | Mooney et al. | |
| 6,852,261 B2 | 2/2005 | Benjamin | |
| 6,866,660 B2 | 3/2005 | Garabedian et al. | |
| 6,881,211 B2 | 4/2005 | Schweikert et al. | |
| 6,939,327 B2 | 9/2005 | Hall et al. | |
| 6,939,337 B2 | 9/2005 | Parker et al. | |
| 7,018,372 B2 | 3/2006 | Casey et al. | |
| 7,025,746 B2 | 4/2006 | Tal | |
| 7,037,295 B2 | 5/2006 | Tiernan et al. | |
| 7,101,353 B2 | 9/2006 | Lui et al. | |
| 7,144,411 B2 | 12/2006 | Ginn et al. | |
| 7,226,433 B2 | 6/2007 | Bonnette et al. | |
| 7,438,712 B2 | 10/2008 | Chouinard | |
| 7,497,844 B2 | 3/2009 | Spear et al. | |
| 7,524,305 B2 | 4/2009 | Moyer | |
| 7,540,865 B2 | 6/2009 | Griffin et al. | |
| 7,628,769 B2 | 12/2009 | Grandt et al. | |
| 7,645,273 B2 | 1/2010 | Lualdi | |
| 7,704,245 B2 | 4/2010 | Dittman et al. | |
| 7,713,260 B2 | 5/2010 | Lessard et al. | |
| 7,722,567 B2 | 5/2010 | Tal | |
| 7,731,694 B2 | 6/2010 | Becker et al. | |
| 7,744,571 B2 | 6/2010 | Fisher et al. | |
| 7,749,185 B2 | 7/2010 | Wilson et al. | |
| 7,766,820 B2 | 8/2010 | Core | |
| 7,833,218 B2 | 11/2010 | Lunn et al. | |
| 7,837,671 B2 | 11/2010 | Eversull et al. | |
| 7,871,398 B2 | 1/2011 | Chesnin et al. | |
| 7,905,877 B1 | 3/2011 | Jimenez et al. | |
| 7,963,948 B2 | 6/2011 | Melsheimer | |
| 7,968,038 B2 | 6/2011 | Dittman et al. | |
| 7,985,213 B2 | 7/2011 | Parker | |
| 7,993,305 B2 | 8/2011 | Ye et al. | |
| 8,123,726 B2 | 2/2012 | Searfoss et al. | |
| 8,206,375 B2 | 6/2012 | Snow | |
| 8,246,574 B2 | 8/2012 | Jacobs et al. | |
| 8,257,298 B2 | 9/2012 | Hamboly | |
| 8,273,059 B2 | 9/2012 | Nardeo et al. | |
| 8,298,189 B2 | 10/2012 | Fisher et al. | |
| 8,317,754 B2 | 11/2012 | Leeflang et al. | |
| 8,343,136 B2 | 1/2013 | Howat et al. | |
| 8,377,035 B2 | 2/2013 | Zhou et al. | |
| 8,398,696 B2 | 3/2013 | Buiser et al. | |
| 8,597,277 B2 | 12/2013 | Lenker et al. | |
| 8,636,270 B2 | 1/2014 | Ostrovsky | |
| 8,672,888 B2 | 3/2014 | Tal | |
| 8,684,963 B2 | 4/2014 | Qiu et al. | |
| 8,728,055 B2 | 5/2014 | Stehr et al. | |
| 8,758,402 B2 | 6/2014 | Jenson et al. | |
| 8,821,510 B2 | 9/2014 | Parker | |
| 8,974,420 B2 | 3/2015 | Searfoss et al. | |
| 9,168,359 B2 | 10/2015 | Rowe et al. | |
| 9,295,809 B2 | 3/2016 | Sheetz | |
| 9,320,873 B2 | 4/2016 | Okamura | |
| 9,352,116 B2 | 5/2016 | Guo et al. | |
| 9,427,551 B2 | 8/2016 | Leeflang et al. | |
| 9,492,636 B2 | 11/2016 | Heideman et al. | |
| 9,539,368 B2 | 1/2017 | Haslinger et al. | |
| 9,539,411 B2 | 1/2017 | Cully et al. | |
| 9,545,496 B2 | 1/2017 | Hiroshige et al. | |
| 9,597,481 B2 | 3/2017 | Ishikawa | |
| 9,622,892 B2 | 4/2017 | Baker et al. | |
| 9,629,978 B2 | 4/2017 | Eversull et al. | |
| 9,707,373 B2 | 7/2017 | Nielsen | |
| 9,901,706 B2 | 2/2018 | Storbeck et al. | |
| 9,937,319 B1 | 4/2018 | Leeflang et al. | |
| 9,980,710 B2 | 5/2018 | Seifert et al. | |
| 9,981,115 B2 | 5/2018 | Merk et al. | |
| 9,987,460 B2 | 6/2018 | Brustad et al. | |
| 10,065,015 B2 | 9/2018 | Leeflang et al. | |
| 10,076,639 B2 | 9/2018 | Guo et al. | |
| 10,086,172 B2 | 10/2018 | Okamura | |
| 2001/0049499 A1 * | 12/2001 | Lui | A61M 39/06 604/164.05 |
| 2002/0058910 A1 | 5/2002 | Hermann et al. | |
| 2002/0072712 A1 | 6/2002 | Nool et al. | |
| 2003/0050604 A1 | 3/2003 | Lui et al. | |
| 2003/0083623 A1 | 5/2003 | Berg et al. | |
| 2004/0059296 A1 | 3/2004 | Godfrey | |
| 2004/0122360 A1 | 6/2004 | Waldhauser et al. | |
| 2004/0267202 A1 | 12/2004 | Potter | |
| 2004/0267203 A1 | 12/2004 | Potter et al. | |
| 2005/0020981 A1 | 1/2005 | Kurth | |

(56) References Cited

U.S. PATENT DOCUMENTS

| | | |
|---|---|---|
| 2005/0090779 A1* | 4/2005 | Osypka ............ A61M 25/0097 604/160 |
| 2005/0090802 A1 | 4/2005 | Connors et al. |
| 2005/0149105 A1 | 7/2005 | Leeflang et al. |
| 2005/0182387 A1 | 8/2005 | Webler |
| 2006/0095050 A1 | 5/2006 | Hartley et al. |
| 2006/0111614 A1 | 5/2006 | Saadat et al. |
| 2006/0135981 A1 | 6/2006 | Lenker et al. |
| 2006/0149293 A1 | 7/2006 | King et al. |
| 2006/0161135 A1 | 7/2006 | VanDerWoude |
| 2006/0200110 A1 | 9/2006 | Lentz et al. |
| 2006/0287574 A1 | 12/2006 | Chin |
| 2007/0225659 A1* | 9/2007 | Melsheimer ...... A61M 25/0668 604/264 |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0306442 A1 | 12/2008 | Bardsley et al. |
| 2009/0143739 A1 | 6/2009 | Nardeo et al. |
| 2009/0240202 A1 | 9/2009 | Drasler et al. |
| 2009/0287187 A1* | 11/2009 | Legaspi ............ A61M 25/0054 604/523 |
| 2010/0082000 A1 | 4/2010 | Honeck et al. |
| 2010/0204655 A1* | 8/2010 | Melsheimer .......... A61M 39/06 604/167.03 |
| 2010/0228178 A1 | 9/2010 | McGraw |
| 2010/0241083 A1 | 9/2010 | Fisher et al. |
| 2010/0268196 A1 | 10/2010 | Hastings et al. |
| 2010/0305509 A1 | 12/2010 | Osypka et al. |
| 2010/0312190 A1 | 12/2010 | Searfoss et al. |
| 2011/0054405 A1* | 3/2011 | Whiting ............ A61B 17/3462 604/167.03 |
| 2011/0270196 A1* | 11/2011 | Valaie ................ A61M 25/0668 604/171 |
| 2012/0245527 A1 | 9/2012 | Stephens et al. |
| 2012/0271236 A1* | 10/2012 | Bruszewski ...... A61M 39/0613 604/167.03 |
| 2013/0072956 A1 | 3/2013 | Searfoss et al. |
| 2013/0131718 A1 | 5/2013 | Jenson et al. |
| 2013/0150793 A1* | 6/2013 | Beissel ............ A61M 25/0105 604/171 |
| 2013/0310765 A1 | 11/2013 | Stephens et al. |
| 2013/0317438 A1 | 11/2013 | Ellingwood et al. |
| 2013/0317481 A1 | 11/2013 | Ellingwood et al. |
| 2015/0051541 A1 | 2/2015 | Kanemasa et al. |
| 2015/0201963 A1 | 7/2015 | Snow |
| 2015/0352330 A1 | 12/2015 | Wasdyke et al. |
| 2016/0001042 A1 | 1/2016 | Worley et al. |
| 2016/0051798 A1 | 2/2016 | Weber et al. |
| 2016/0058976 A1 | 3/2016 | Okamura et al. |
| 2016/0066948 A1 | 3/2016 | Ellingwood et al. |
| 2016/0096000 A1 | 4/2016 | Mustapha |
| 2016/0220358 A1 | 8/2016 | Wilson et al. |
| 2016/0346507 A1 | 12/2016 | Jackson et al. |
| 2016/0346508 A1 | 12/2016 | Williams et al. |
| 2016/0354583 A1 | 12/2016 | Ellingwood et al. |
| 2016/0375222 A1 | 12/2016 | Vada |
| 2017/0043135 A1 | 2/2017 | Knutsson |
| 2017/0056063 A1 | 3/2017 | Ellingwood et al. |
| 2017/0065267 A1* | 3/2017 | Fantuzzi ............... A61M 39/06 |
| 2017/0072165 A1 | 3/2017 | Lim et al. |
| 2017/0113018 A1 | 4/2017 | Shimizu et al. |
| 2017/0120008 A1 | 5/2017 | Burkholz et al. |
| 2017/0238965 A1 | 8/2017 | Murphy |
| 2017/0252535 A1 | 9/2017 | Ganske et al. |
| 2017/0281908 A1 | 10/2017 | Ellingwood et al. |
| 2017/0296777 A1 | 10/2017 | Heisel et al. |
| 2017/0333682 A1 | 11/2017 | Nardeo |
| 2017/0340860 A1 | 11/2017 | Eberhardt et al. |
| 2018/0001061 A1 | 1/2018 | Okamura et al. |
| 2018/0015254 A1 | 1/2018 | Cragg et al. |
| 2018/0043138 A1 | 2/2018 | Chu |
| 2018/0056037 A1 | 3/2018 | Shimizu |
| 2018/0161540 A1* | 6/2018 | Fantuzzi ........... A61M 25/0014 |
| 2018/0250498 A1 | 9/2018 | Stern et al. |
| 2018/0256847 A1 | 9/2018 | Lareau et al. |
| 2018/0361116 A1 | 12/2018 | Quick et al. |
| 2019/0351194 A1* | 11/2019 | Korkuch ............... A61M 39/02 |

FOREIGN PATENT DOCUMENTS

| | | |
|---|---|---|
| EP | 1444000 A2 | 8/2004 |
| EP | 2335764 A1 | 6/2011 |
| EP | 3347079 A1 | 7/2018 |
| JP | 4695878 B2 | 6/2011 |
| JP | 2011130846 A | 7/2011 |
| JP | 5581139 B2 | 8/2014 |
| WO | WO-93/08986 A1 | 5/1993 |
| WO | WO-93/15872 A1 | 8/1993 |
| WO | WO-97/37713 A1 | 10/1997 |
| WO | WO-00/48659 A2 | 8/2000 |
| WO | WO-01/41858 A2 | 6/2001 |
| WO | WO 2009/114556 | 9/2009 |
| WO | WO-2017/094697 A1 | 6/2017 |
| WO | WO-2018/191547 A1 | 10/2018 |

OTHER PUBLICATIONS

International Preliminary Report on Patentability and Written Opinion for application No. PCT/US2018/059486 dated May 22, 2020.
International Search Report and Written Opinion for International Application No. PCT/US2018/059486 dated Apr. 30, 2019.

* cited by examiner

1300

```
┌─────────────────────────────────────────┐
│  Apply a first force to a first wing of hub and a  │
│  second force to a second wing of hub   │
└─────────────────────────────────────────┘
                    1302
                     ↓
┌─────────────────────────────────────────┐
│  Causing the first and second forces to be         │
│  transmitted to a first notch and a second notch of│
│  the hub, breaking the first and second notches    │
└─────────────────────────────────────────┘
                    1304
                     ↓
┌─────────────────────────────────────────┐
│  Causing a hemostasis valve of the hub to break    │
│  along a first longitudinal cut and a second       │
│  longitudinal cut                       │
└─────────────────────────────────────────┘
                    1306
                     ↓
┌─────────────────────────────────────────┐
│  Separate an introducer sheath along a  │
│  longitudinal scoring on the sheath     │
└─────────────────────────────────────────┘
                    1308
```

FIG. 13

PEEL AWAY HEMOSTASIS VALVE

CROSS-REFERENCE TO RELATED APPLICATION

This application claims the benefit of U.S. Provisional Application No. 62/582,075, filed on Nov. 6, 2017, the content of which is hereby incorporated herein by reference in its entirety.

FIELD OF THE INVENTION

The present disclosure relates to systems and methods for implementing a peel away hemostasis valve.

BACKGROUND

An introducer sheath is used for the percutaneous insertion of medical devices such as heart pumps, guidewires, and diagnostic catheters into an artery or vein of a patient. A hemostasis valve and a hub are parts of the introducer sheath that are designed to have medical devices inserted through and be able to be removed in-line from the inserted medical devices. During the insertion of the medical devices, hemostasis valves should resist tearing while maintaining hemostasis. In addition, the hemostasis valve may split into two pieces with acceptable force during a peel away action of the introducer sheath.

Some peel away hemostasis valve designs have a thickness that helps with sealing but requires high force to tear. Other peel away hemostasis valve designs are cut all the way through the thickness of the valve body to provide low forces for tearing but have trouble sealing around the medical devices used throughout the procedure. However, many current peel away hemostasis valves do not exhibit the performance necessary for the insertion of modern heart pump systems.

In addition to sealing performance and ease of peel away, hemostasis valves should also allow for stability during insertion of heart pump systems as well as during peel away. Some peel away hemostasis valve designs suffer from a double break during peel away, which occurs when the valve has two distinct points of resistance to tearing. For example, the double break points may be located near the edge of the valve and at the center of the valve. A double break causes movement of the heart pump system while in the artery or vein of the patient and can cause damage to the arteriotomy of the patient and/or damage to the heart pump system. There is a need for a hemostasis valve design that mitigates double breaks during peel away and improves the stability of the heart pump system placement during a procedure.

SUMMARY OF INVENTION

The systems, methods, and devices described herein provide for a peel away hemostasis valve designed in a manner to provide low forces for tearing, strong sealing around the medical devices, and stability during insertion of the medical devices as well as during peel away. The valve of the present disclosure has longitudinal cuts that are defined by a cylindrical surface axially aligned with the outer diameter of the hemostasis valve and an edge that aligns with the spiral path of one of the helical slits at the center of the hemostasis valve. Compared with existing valves, the design of the longitudinal cuts in the valve of the present disclosure reduces the required force to tear through the peel away hemostasis valve during a peel away action. The longitudinal cuts and the helical slits are separated by a constant distance through the thickness of the valve, which provides better hemostasis performance compared to a hemostasis valve that has longitudinal cuts all the way through the valve. The peel away hemostasis valve of the present disclosure also has through holes along its perimeter that facilitate connection of the hemostasis valve to the hub of an introducer and maintains a stretch (when posts are inserted in the through holes) in the hemostasis valve during a peel away action.

Embodiments are disclosed herein for a hemostasis valve body comprising a first surface, a second surface opposite the first surface, an edge, helical slits, and a pair of longitudinal cuts. The edge extends between the outer perimeters of the first surface and the second surface. The helical slits are positioned at a center of the valve body and traverse the first surface to the second surface. The helical slits provide a seal around a medical device during an insertion of the medical device into a blood vessel. Each respective longitudinal cut extends from the first surface partially through the valve body to a depth short of the second surface for at least part of a length of the respective longitudinal cut. The longitudinal cuts facilitate a separation of the valve body into two parts during a peel away action. The embodiments disclosed herein provide a peel away hemostasis valve that seals well to a medical device inserted therein and also allows for peeling away the hemostasis valve with low force. Additionally, the design of the peel away hemostasis valve prevents a double break and facilitates stability of medical devices or heart pump systems during procedures.

In certain implementations, the longitudinal cuts may be positioned at a distance from the helical slits. According to some implementations, the longitudinal cuts may be angled at a similar angle of rotation as the helical slits. In certain implementations, each respective longitudinal cut may be positioned on opposite sides of the valve body. According to some implementations, each respective longitudinal cut may traverse the first surface to the second surface for at least part of the length of the respective longitudinal cut near the edge.

According to one implementation, the hemostasis valve body may comprise a first group of lines formed on the first surface and a second group of lines formed on the second surface. The first group of lines may extend radially outward from the center of the valve. The second group of lines may extend radially outward from the center of the valve. In some implementations, the helical slits may traverse the first group of lines to the second group of lines. According to some implementations, the first group of lines may be angularly offset from the second group of lines.

In certain implementations, the hemostasis valve body may comprise through holes at a distance from the edge that traverse the first surface to the second surface. According to some implementations, each respective through hole may comprise one of round edges, flat edges, and non-symmetric shape. In some implementations, the through holes may be angularly spaced equally. According to certain implementations, the angle between adjacent through holes may be less than or equal to 25 degrees. In other implementations, the through holes may be sized to accommodate ports. According to some implementations, the through holes (when posts are inserted therethrough) may keep the hemostasis valve body stretched during a peel away action.

According to one implementation, the first surface may be parallel to the second surface. In some implementations, the first surface and the second surface may comprise a planar shape. According to some implementations, the first surface may comprise one of a conical, tapered, and convex shape.

In certain implementations, a shallow point of the first surface may be at the center of the valve.

According to some implementations, the valve body may comprise a disc shape. According to one implementation, the valve body may comprise one of a cylindrical and cubic shape.

According to a further implementation of the present disclosure, a system is provided for inserting a blood pump into a blood vessel of a patient. The system includes a blood pump and an introducer assembly, which comprises a sheath and a hub that includes the hemostasis valve body. The sheath and the hemostasis valve body can be sized to receive the blood pump. The introducer hub includes wings and notches that facilitate the breaking of the introducer hub. A medical service professional applies force on the wings in order to break the introducer hub during a peel away action. The notches are purposefully implemented as weak points on the hub that break when sufficient force is applied on the wings. The longitudinal cuts on the hemostasis valve body can be radially aligned with the notches in order for the valve to break without much force along the longitudinal cuts.

According to a further implementation of the present disclosure, a method is provided for peeling away an introducer sheath assembly having (1) an introducer hub, the introducer hub having (a) first and second wings located opposite each other, and (b) first and second notches located at midpoints between the first and second wings, (2) a hemostasis valve within the introducer hub having first and second longitudinal cuts radially aligned with the first and second notches, and (3) a introducer sheath having longitudinal scoring aligned with the first and second notches. As described above, the wings and notches facilitate the breaking of the introducer hub. Compared with other peel away methods, this method achieves a smooth peel away along a consistent tearing path by aligning purposefully implemented weak points on the introducer hub, hemostasis valve, and introducer sheath. The method comprises applying a first force to the first wing of the introducer hub in a first direction radial from an introducer sheath and a second force to the second wing of the introducer hub in a second direction opposite the first direction. The method further comprises causing the first force and the second force to be transmitted to the first and second notches of the introducer hub, thereby breaking the first and second notches. The method further comprises causing the hemostasis valve to break along the first and second longitudinal cuts. The method further comprises separating the introducer sheath along the longitudinal scoring.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 13 shows a flowchart for peeling away an introducer having a peel away hemostasis valve, configured according to one or more aspects of the present disclosure.

DETAILED DESCRIPTION

There is a need for a peel away hemostasis valve that seals well and has features allowing for peeling away the hemostasis valve with low force. The peel away hemostasis valve described herein accomplishes this by incorporating longitudinal cuts that are defined by a cylindrical surface axially aligned with the outer diameter of the hemostasis valve and an edge that aligns with the spiral path of one of the helical slits at the center of the hemostasis valve. The design of the longitudinal cuts lowers the required force to tear through the peel away hemostasis valve during a peel away action. The longitudinal cuts and the helical slits are separated by a constant distance which provides better hemostasis performance compared to a hemostasis valve that is cut all the way through. Additionally, there is a need for a peel away hemostasis valve that does not double break and facilitates stability of heart pump systems during procedures. The peel away hemostasis valve described herein accomplishes this by incorporating through holes along the perimeter of the hemostasis valve that connect the hemostasis valve to the hub of an introducer and keeps the hemostasis valve stretched (when posts are inserted through the through holes) during a peel away.

Figure 1:
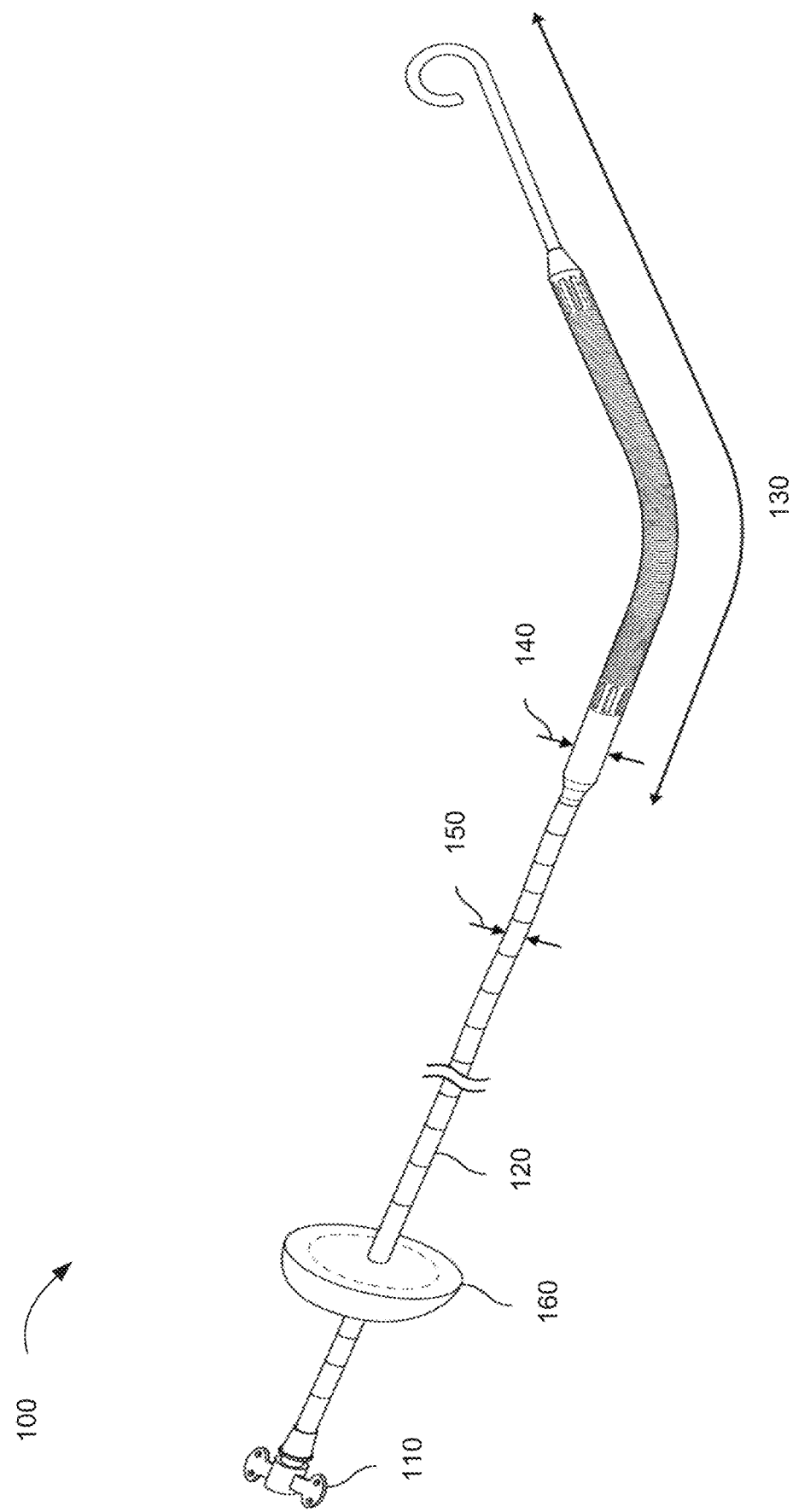
FIG. 1 shows an illustrative medical device, configured according to one or more aspects of the present disclosure.

FIG. 1 shows an illustrative medical device such as a blood pump 100 according to certain implementations. The blood pump 100 may be an intravascular heart pump, a heart pump driven by a flexible shaft and a motor positioned external to the patient's body, a heart pump including an implantable motor, a heart pump having an expandable pump rotor, or any other suitable pump. The blood pump 100 comprises a pump handle 110, a pump head 130, a catheter 120 connecting the pump handle 110 to the pump head 130, and a connecting hub 160. The catheter 120 is tubular and has a substantially uniform outer diameter 150. The catheter 120 enables the pump head 130 and the pump handle 110 to be in electro-mechanical communication. The pump handle 110 is in communication with control circuitry which allows the control of the pump head 130. The pump head 130 contains electro-mechanical components that enable the device to perform various tasks within the body of a patient, such as pump blood from a location within the body. The pump head 130 has a diameter 140 that is larger than the diameter 150 of the catheter 120. An example of such a percutaneous pump is the Impella 2.5® system (Abiomed, Inc., Danvers, Mass.).

Figure 2:
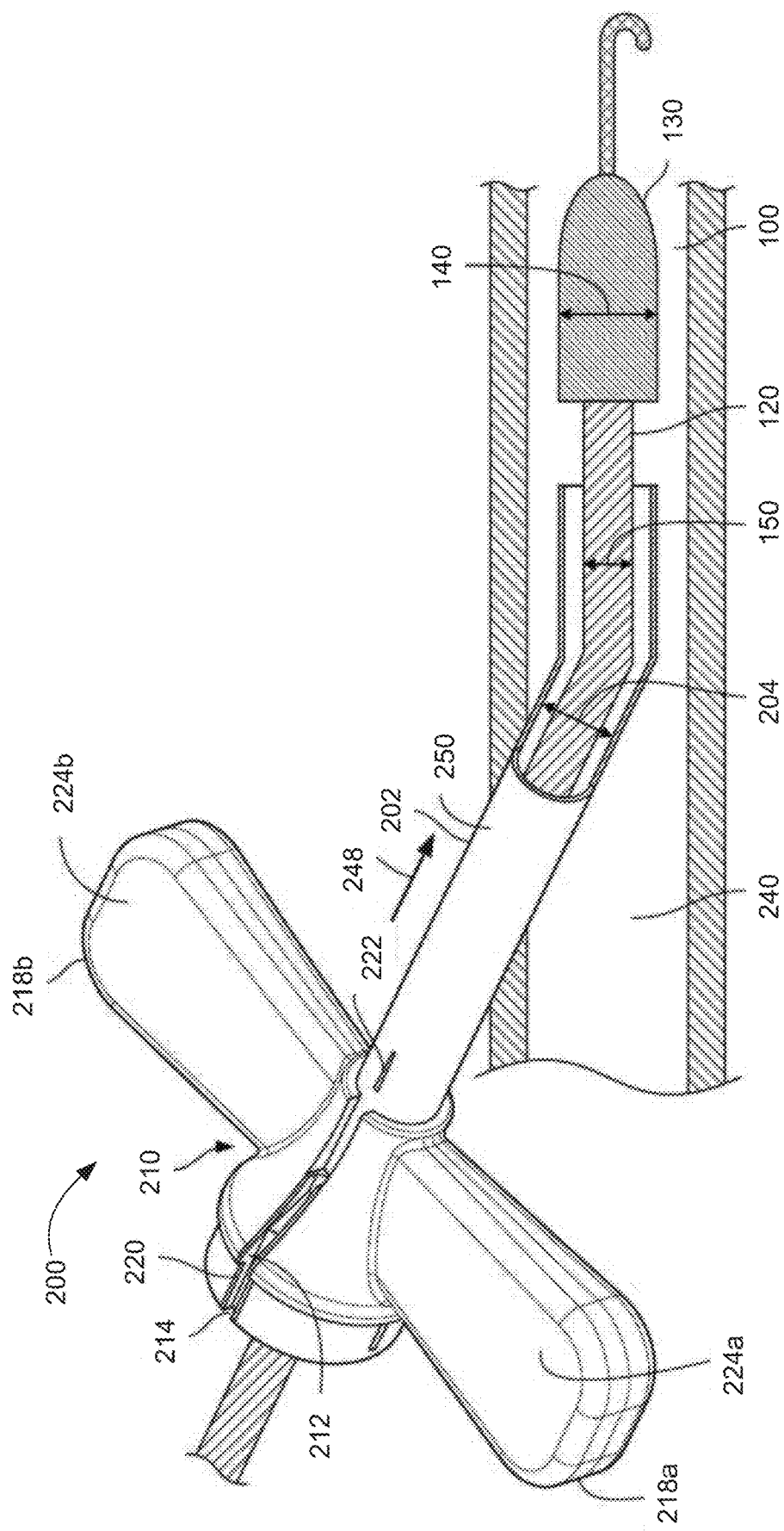
FIG. 2 shows an illustrative introducer inserted into a blood vessel of a patient with the medical device of FIG. 1 extending therethrough, configured according to one or more aspects of the present disclosure.

As depicted in FIG. 2, the blood pump 100 is inserted into a blood vessel 240 of a patient using an introducer 200. The introducer 200 includes a hub 210 and an elongate sheath 202. The hub 210 includes hemostasis valve 300 (described further below) which provides a seal and minimizes fluid loss during the insertion of the blood pump 100. The elongate sheath 202 is sized for insertion into the blood vessel 240 of a patient. The introducer 200 is advanced into the blood vessel 240 through a blood vessel aperture 250 in the direction indicated by arrow 248 and then the blood pump 100 is inserted through the hub 210 and elongate sheath 202, and into the blood vessel 240. The blood vessel 240 may be a femoral artery, and the blood vessel aperture 250 may be an arteriotomy.

After the blood pump 100 has been advanced through the introducer 200, the introducer 200 may be removed and, in some implementations, replaced by a device appropriate for longer-term use. To remove the introducer 200, a healthcare professional may grasp first and second wings 218a and 218b of the hub 210, and apply a force to the wings 218a and 218b in a direction either toward the elongate sheath 202 or a direction radial to the elongate sheath 202, forcing the first wing 218a toward the second wing 218b depending on the orientations of the first and second wings 218a and 218b relative to the elongate sheath 202. In the orientation of wings 218a and 218b as shown in FIG. 2, the healthcare professional applies a radial force (radial with respect to the elongate sheath 202) to the wings 218a and 218b to move them toward each other. The first and second wings 218a and 218b are formed of a stiff material and do not flex when force is applied. Instead, the applied force is transmitted from the wings 218a and 218b to a first notch 214 and second notch (not shown) on the introducer hub 210. The second notch is located opposite the first notch 214, and both of the first notch 214 and second notch are located at a midpoint between the first and second wings 218a and 218b. The minimum thicknesses at the notches allows the introducer 200 to break at the first notch 214 and second notch. The longitudinal scoring 222 on the elongate sheath 202 allows the sheath to separate along the length of the elongate sheath, and the hub 210 and elongate sheath 202 may be peeled away in two pieces leaving the percutaneous pump 100 in place in the blood vessel 240.

Figure 3:
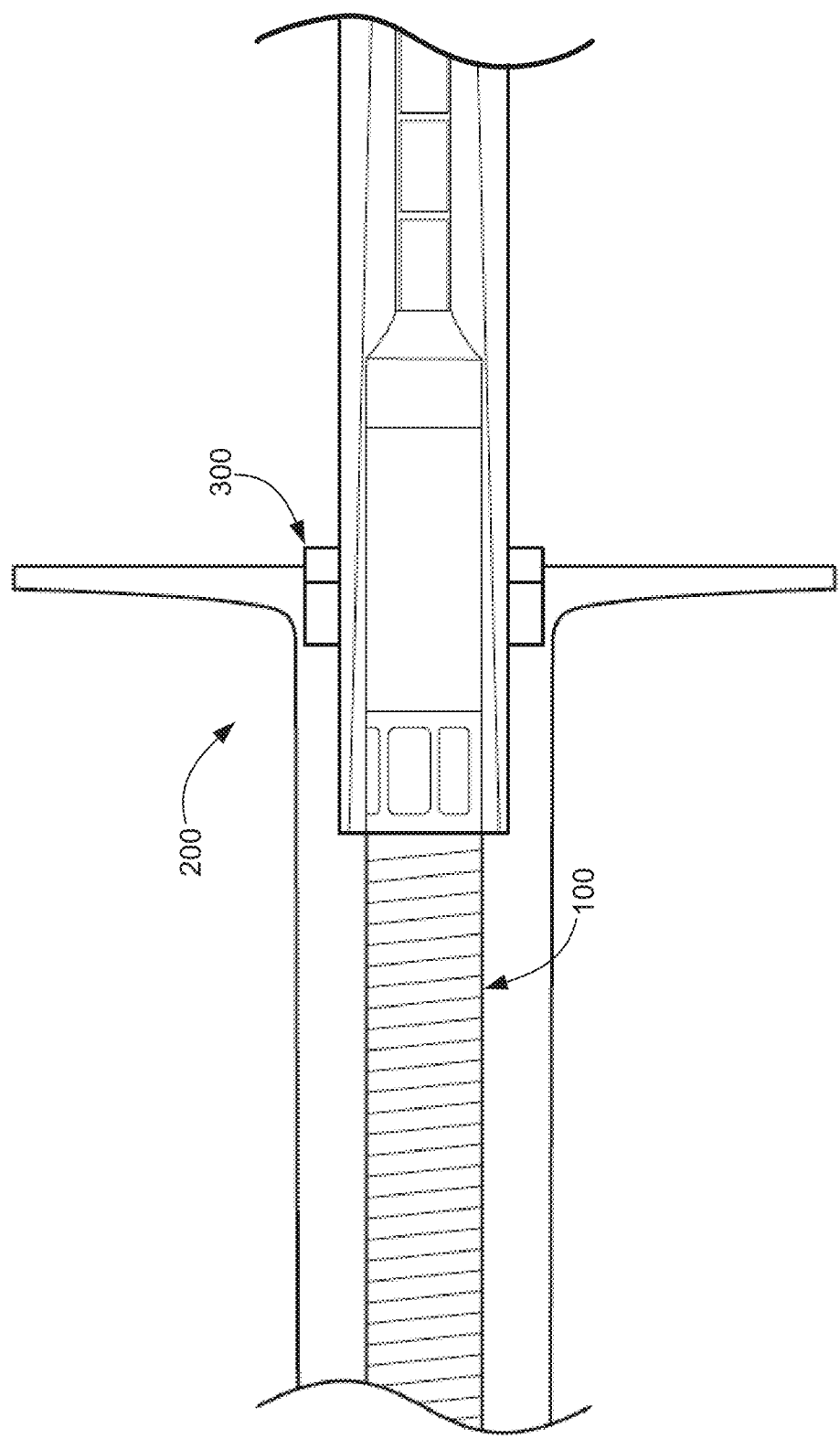
FIG. 3 shows a cross-section of the medical device of FIG. 1 inserted into a peel away hemostasis valve of the introducer of FIG. 2, configured according to one or more aspects of the present disclosure.

FIG. 3 shows a cross-section of the blood pump 100 of FIG. 1 inserted into the introducer 200 of FIG. 2. The hub 210 of introducer 200 includes hemostasis valve 300 that provides a seal and minimizes fluid loss during the insertion of the blood pump 100. The hemostasis valve 300 described in FIGS. 4-8 seals well and has features allowing for peeling away the peel away hemostasis valve with low force as described below.

Figure 4:
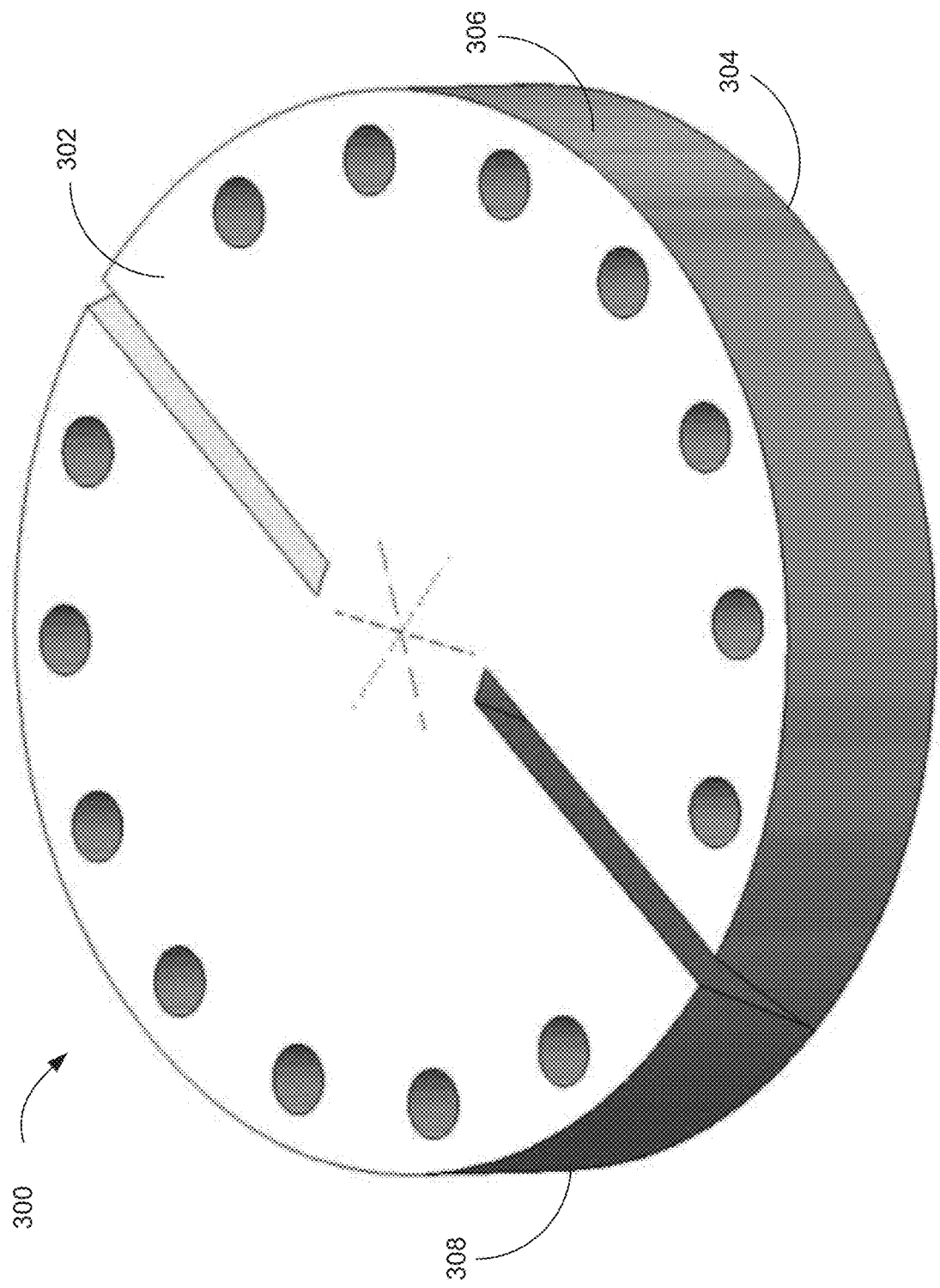
FIG. 4 shows an isometric view of a peel away hemostasis valve, configured according to one or more aspects of the present disclosure.

FIG. 4 shows an isometric view of a peel away hemostasis valve 300. Peel away hemostasis valve 300 includes first surface 302, second surface 304 that is opposite and parallel to the first surface 302, and edge 306 that extends between the outer perimeters of the first surface 302 and the second surface 304.

As depicted in FIG. 4, peel away hemostasis valve 300 has a disc shape, in which the first surface 302 and the second surface 304 are planar and circular, and the edge 306 extends perpendicularly from each of the first and second surfaces 302 and 304. In general, the peel away hemostasis valve 300 may take on other shapes, including but not limited to cylindrical or cubic shape. A disc shape may be a subset of a cylinder whereby the ratio of the thickness of edge 306 to the diameter of the first surface 302 is less than 1. In general, the shapes of the first surface 302 and the second surface 304 may be any suitable shape, such as a triangle, square, pentagon, hexagon, or any other polygon. While the first surface 302 and the second surface 304 are depicted in FIG. 4 as being planar surfaces, the surfaces 302 and 304 may include any combination of conical, tapered, convex, concave, or planar. In particular, the thickness of the valve 308 (i.e., the distance between respective points on the surfaces 302 and 304) may vary throughout the valve body. For example, the valve may be thinnest at its center, such that one or both of surfaces 302 and 304 may include a shallow point at its center.

The thickness 308 of the peel away hemostasis valve 300 may be set to achieve the specific hemostasis performance required. The hemostasis performance of the peel away hemostasis valve is improved if the thickness 308 of the peel away hemostasis valve 300 is set to a large value. In another aspect, the thickness 308 of the peel away hemostasis valve 300 may be set to require a certain amount of force during a peel away action. The amount of force required during a peel away action is small if the thickness 308 of the peel away hemostasis valve 300 is set to a small value. In some aspects, the thickness 308 of the peel away hemostasis valve 300 may be set to satisfy a tradeoff between the specific hemostasis performance and the required amount of force during a peel away action.

Peel away hemostasis valve 300 may be inserted into the vasculature by an introducer sheath. Peel away hemostasis valve 300 may have medical devices inserted through and may be able to be removed in-line from the inserted medical devices. The medical devices may include heart pumps, guidewires, diagnostic catheters, sheaths, and dilators.

Figure 5:
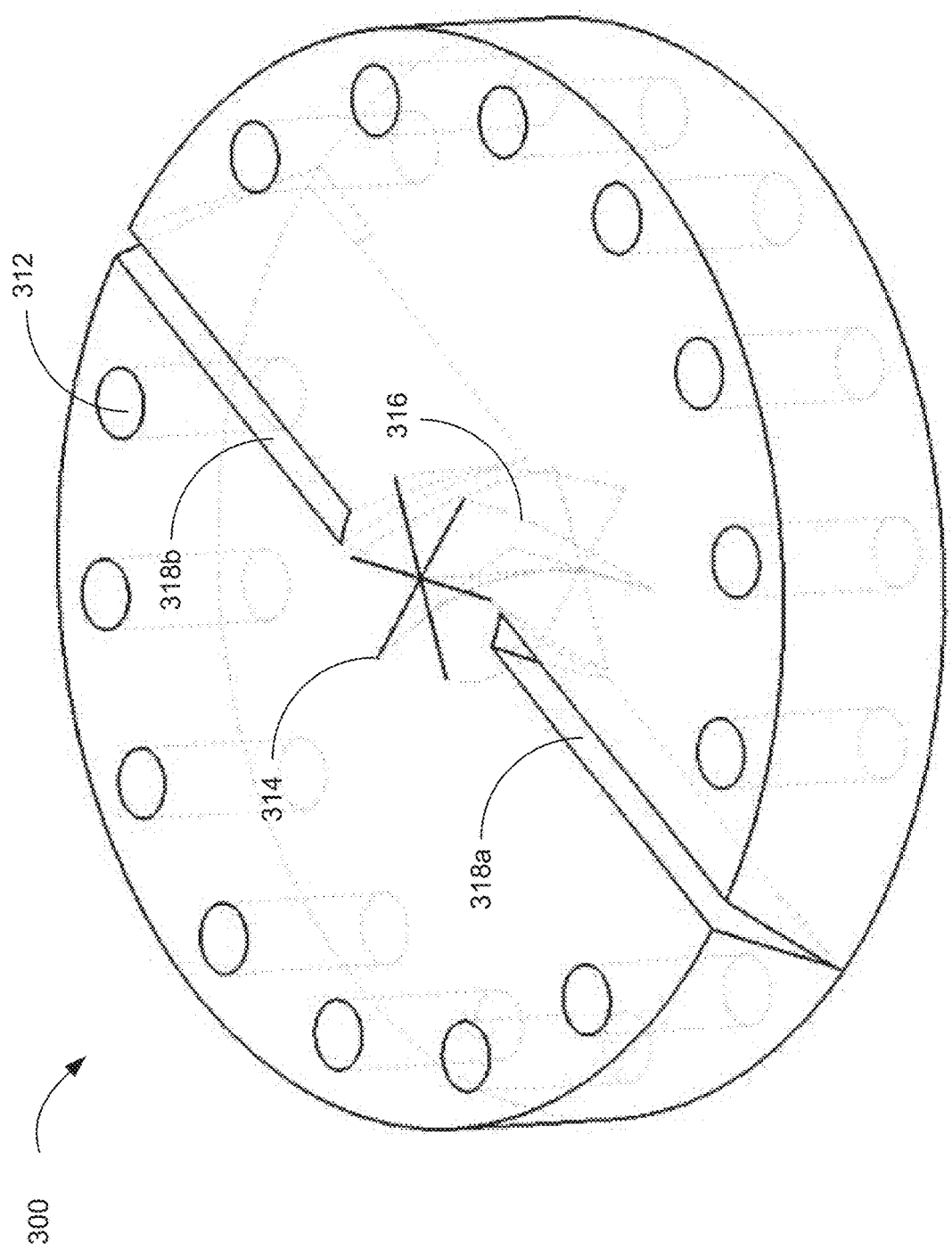
FIG. 5 shows an isometric view of a peel away hemostasis valve with hidden lines, configured according to one or more aspects of the present disclosure.
Figure 6:
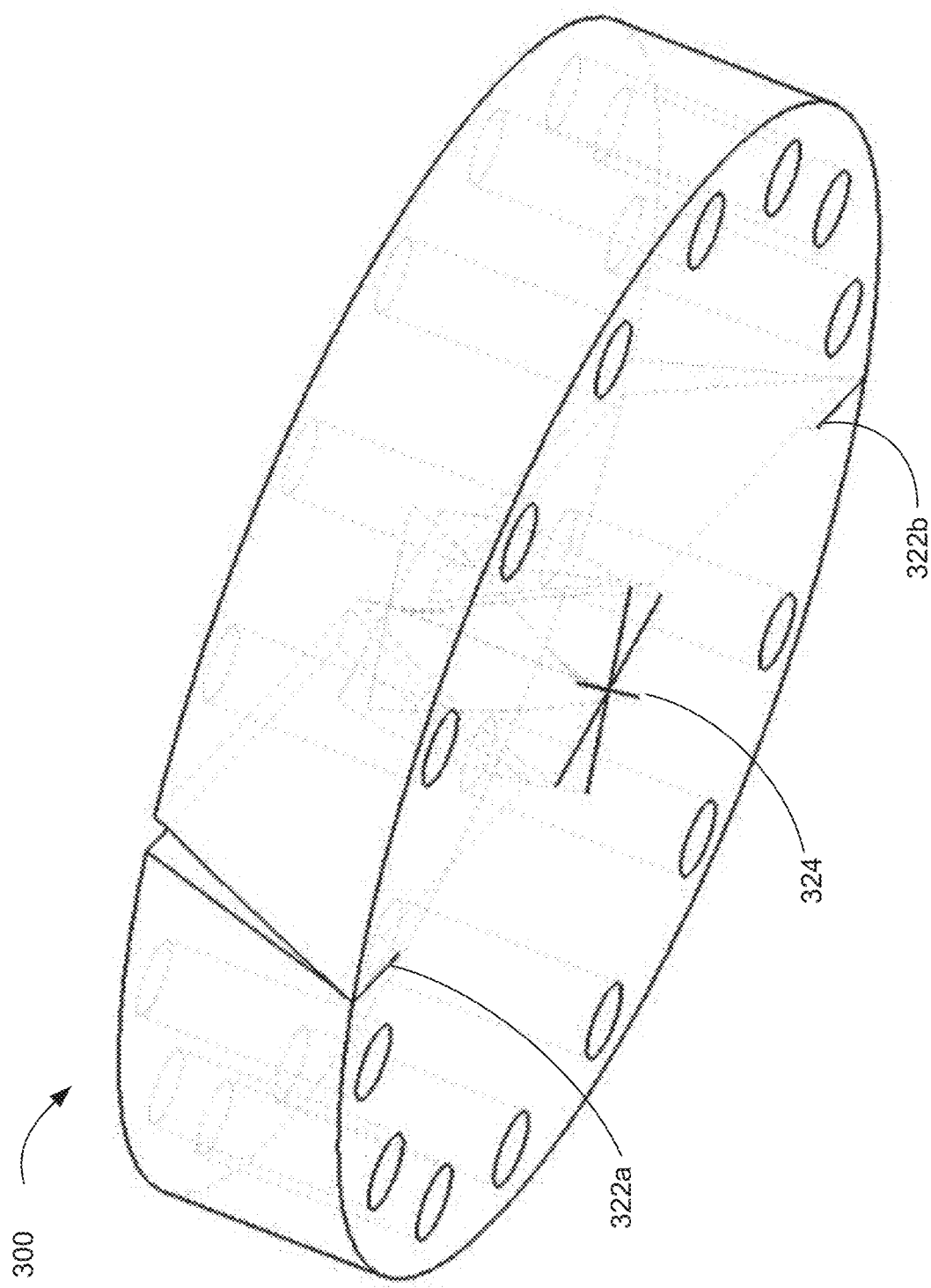
FIG. 6 shows a bottom view of a peel away hemostasis valve, configured according to one or more aspects of the present disclosure.

FIG. 5 shows an isometric view of a peel away hemostasis valve 300 with hidden dotted lines, which depict cuts present in the valve. FIG. 6 shows a bottom view of the peel away hemostasis valve 300. Peel away hemostasis valve 300 includes through holes 312 positioned along the periphery of the valve, first group of lines 314 at the center of the valve at the top surface, second group of lines 324 at the center of the valve at the bottom surface, helical slits 316 extending through the center of the valve, longitudinal cuts 318a and 318b positioned on opposite sides of the valve and extending away from each other, and through slits 322a and 322b.

As depicted in FIGS. 5 and 6, the first group of lines 314 are formed on first surface 302, include three diameter cuts with the same center, and extend radially outward from the center of peel away hemostasis valve 300. A second group of lines 324 are formed on second surface 304 and have the same shape as the first group of lines 314. The first group of lines 314 and the second group of lines 324 have a snowflake shape. The snowflake shape may have four-fold radial symmetry, six-fold radial symmetry, eight-fold radial symmetry, or any other suitable radial symmetry. The angular offset between the lines in the snowflake shape may be 90°, 60°, 45°, 30°, or any other suitable angle. In another aspect, the snowflake shape may not have radial symmetry.

Helical slits 316 traverse through the center of the valve from the first group of lines 314 in the first surface 302 to the second group of lines 324 in the second surface 304. The helical slits 316 follow a spiral path between first surface 302 and second surface 304. The length of the first group of lines 314 and the second group of lines 324 determines the size of the helical slits 316. The size of the helical slits 316 may be set to balance the hemostasis performance with the insertion and removal force of the medical devices inserted through the peel away hemostasis valve 300. As the length of the first group of lines 314 and the second group of lines 324 increases, the size of the helical slits 316 increases, the hemostasis performance of the peel away hemostasis valve 300 decreases, and the removal force of the medical devices inserted through the peel away hemostasis valve 300 decreases.

Each longitudinal cut 318a and 318b may extend from first surface 302 partially through the peel away hemostasis valve 300 to a depth short of second surface 304 for at least part of a length of the respective longitudinal cut 318a or 318b.

Longitudinal cuts 318a and 318b facilitate a separation of the peel away hemostasis valve 300 into two parts during a peel away action. Longitudinal cuts 318a and 318b may be positioned at a distance from helical slits 316. Each longitudinal cut 318a and 318b may be positioned on opposite sides of the peel away hemostasis valve 300. Each longitudinal cut 318a and 318b may traverse first surface 302 to second surface 304 for at least part of the length of the respective longitudinal cut 318a or 318b near edge 306. The region where the longitudinal cut 318a or 318b traverses through the entire thickness 308 of the hemostasis valve 300 is referred to herein as a through slit 322a or 322b, which may serve as an origin for tear propagation during a peel away action. The termination of the longitudinal cuts 318a and 318b at the first surface 302 of the peel away hemostasis valve 300 may be a sharp edge.

Figure 7:
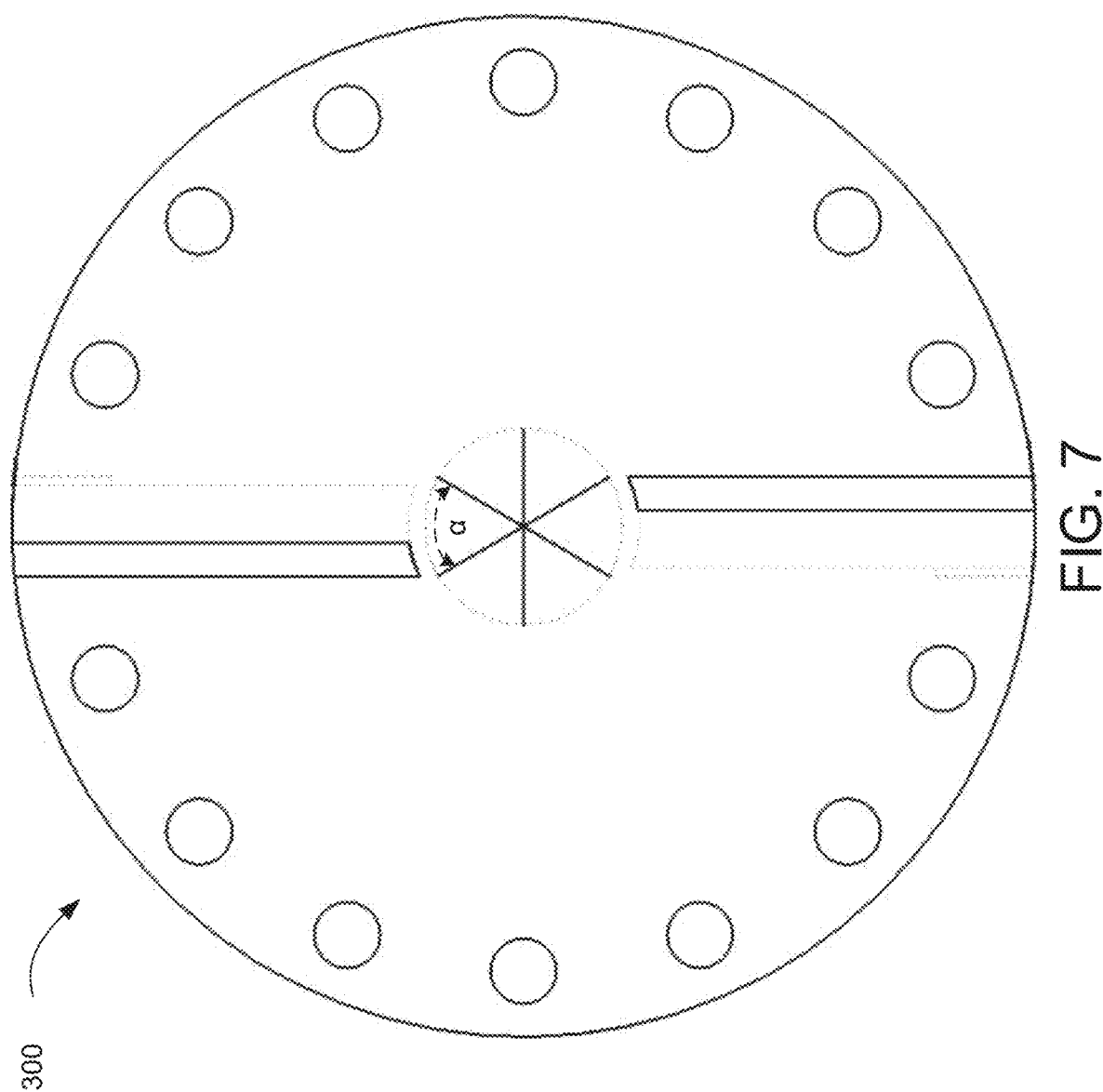
FIG. 7 shows a top view of a peel away hemostasis valve, configured according to one or more aspects of the present disclosure.
Figure 8:
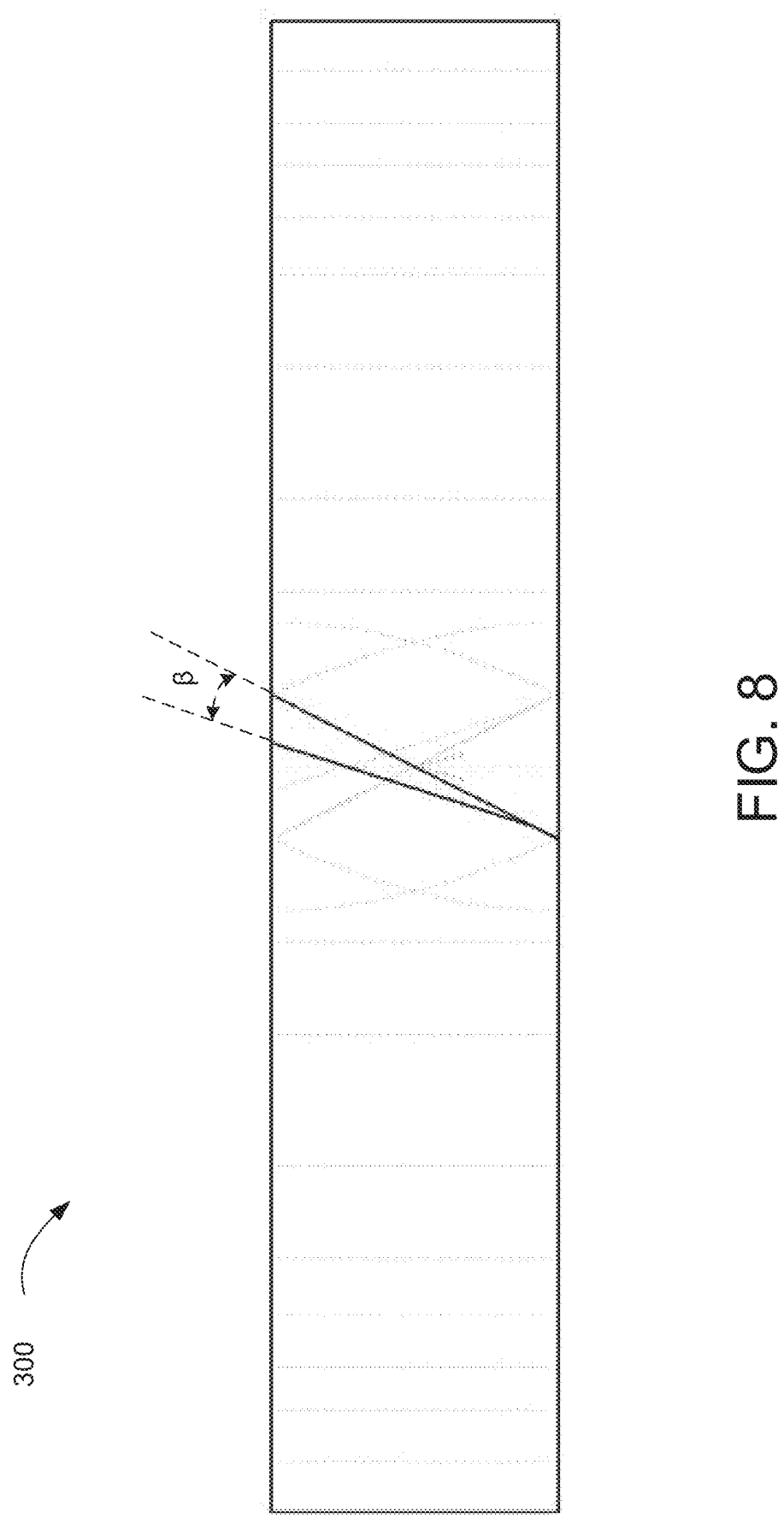
FIG. 8 shows a side view of a peel away hemostasis valve, configured according to one or more aspects of the present disclosure.

In some embodiments, longitudinal cuts 318a and 318b are angled at a similar angle of rotation as the helical slits 316. As depicted in FIG. 7, the angle $\alpha$ of the helical slits 316 defines an angular path the helix slits 316 go through as they traverse the valve 300 from the first surface 302 to the second surface 304. In general, $\alpha$ can be any angle that matches the angular offset between the first group of lines 314 on the first surface 302 and the second group of lines 324 on the second surface 304. In another aspect, the angle $\alpha$ matches the angular offset of two of the helical slits 316 on the first surface 302. In some aspects, $\alpha$ is equal to 360/n, where n is a number of helical slits 316. In another aspect, $\alpha$ is not related to the angular offset of two of the lines 314 on the first surface 302. In this case, $\alpha$ is the angle of rotation of the helix between the first and second surfaces 302 and 304, and need not correspond to an angle between two lines 314, such that the first group of lines 314 and the second group of lines 324 may be angularly offset from each other. As depicted in FIG. 8, the angle $\beta$ of the longitudinal cuts 318a and 318b defines the angle between the two faces of each longitudinal cut 318a and 318b. The angles $\alpha$ and $\beta$ may be related to each other. In some aspects, $\alpha$ and $\beta$ are within 5%, 10%, or 15% of each other, or any other suitable percentage. In another aspect, $\alpha$ and $\beta$ are proportional to each other. By aligning longitudinal cuts 318a and 318b with helical slits 316 (i.e., by ensuring that $\alpha$ and $\beta$ are such that the face of the longitudinal cuts 318a and 318b nearest to the corresponding cut in the helical slit 316 follows the path of the corresponding cut in the helical slit 316), a constant distance is maintained between the longitudinal cut 318 and the nearest corresponding cut in the helical slit 316. The constant distance between longitudinal cuts 318a and 318b and helical slits 316 may be set appropriately to fine tune the amount of force required during a peel away action. If the constant distance between longitudinal cuts 318a and 318b and helical slits 316 is set to a high value, a larger force is required during a peel away action.

During a peel away action, a tear starts at the through slits 322a and 322b (located near the edge 306 of the valve) and propagates along the portion of the longitudinal cuts 318a and 318b near the second surface 304. The tear then proceeds to propagates from the second surface 304 to the first surface 302 along the distance between the longitudinal cuts 318a and 318b and the helical slits 166. The tear propagation results in splitting the peel away hemostasis valve 300 into two pieces along the path described.

In certain implementations, peel away hemostasis valve 300 is partially surrounded by the hub 210 of introducer 200 (as described further in relation to FIGS. 11 and 12) and aligned with notches on the hub 210, such that the longitudinal cuts 318a and 318b of peel away hemostasis valve 300 are aligned with the notches. By aligning the longitudinal cuts 318a and 318b with the notches, the user can use a low force to easily split the peel away hemostasis valve 300 into two pieces during a peel away action using the introducer assembly 200.

Figure 9:
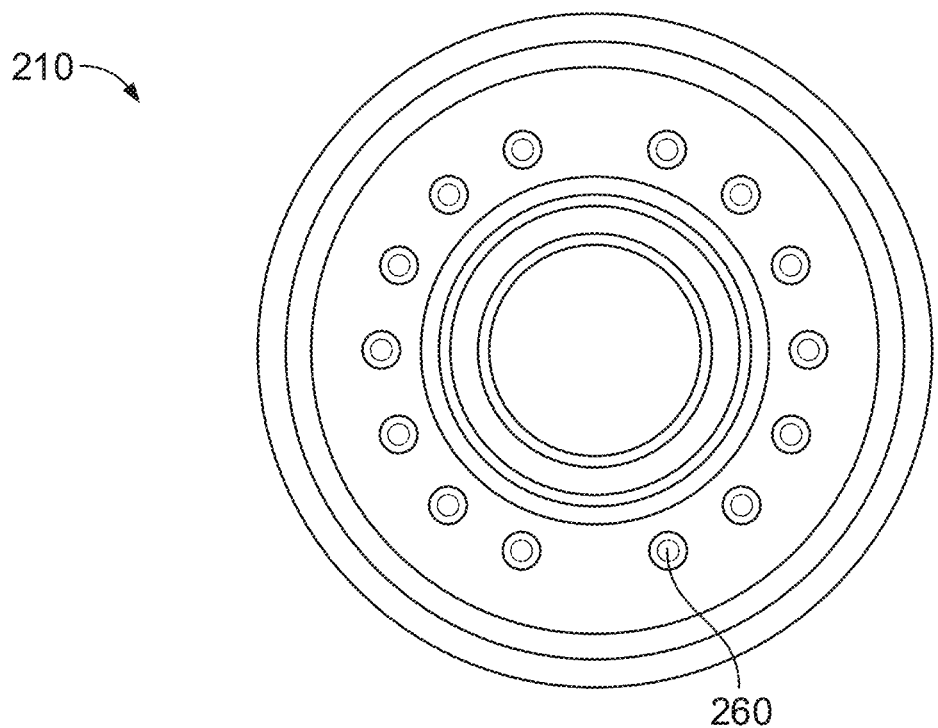
FIG. 9 shows a top view of an introducer hub, configured according to one or more aspects of the present disclosure.
Figure 10:
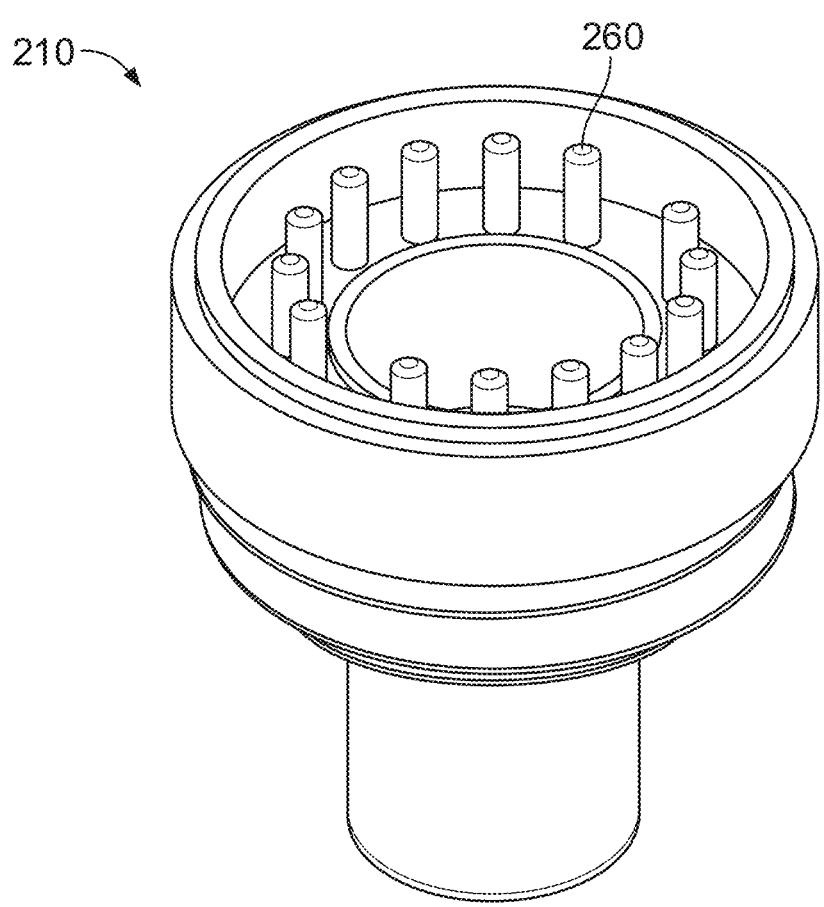
FIG. 10 shows an isometric view of an introducer hub, configured according to one or more aspects of the present disclosure.
Figure 11:
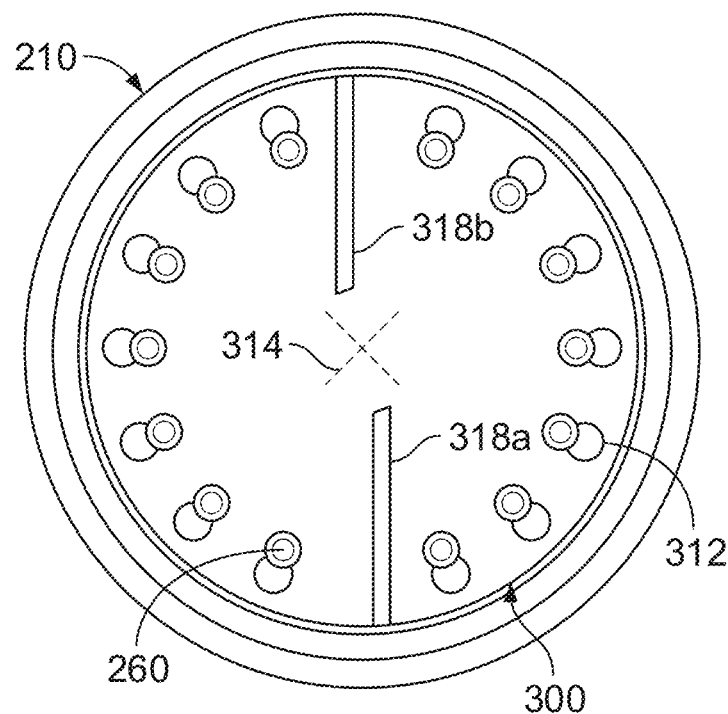
FIG. 11 shows a top view of a peel away hemostasis valve inserted into an introducer hub, configured according to one or more aspects of the present disclosure.
Figure 12:
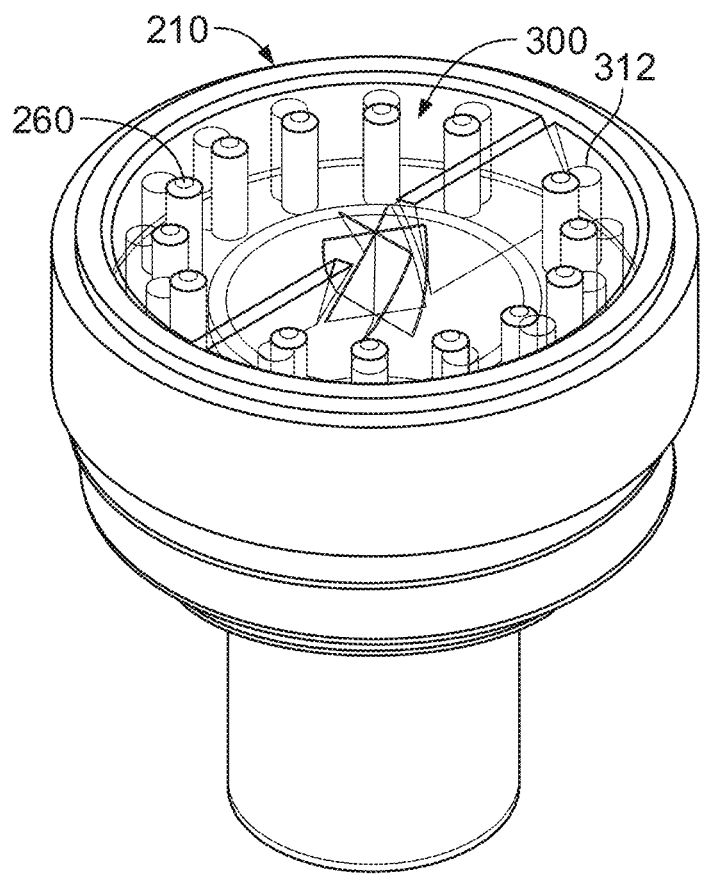
FIG. 12 shows an isometric view of a peel away hemostasis valve inserted into an introducer hub, configured according to one or more aspects of the present disclosure.

FIGS. 9 and 10 show top and isometric views, respectively, of the hub 210 of introducer 200. As shown, hub 210 has posts 260 arranged in a circle around its perimeter and with equal angular spacing between them except for the spacing between the posts 260 nearest to the notches of the hub 210. The angular spacing between the posts 260 nearest to the notches of the hub 210 is larger than the spacing between the other posts 260 because the hub 210 breaks along the notches. The posts 260 in hub 210 extend through the through holes 312 on the valve, such that the posts 260 facilitate anchoring and secure the valve 300 within the hub 210. The through holes 312 are located at a distance from the valve's edge 306 and traverse the first surface 302 to the second surface 304. While the through holes 312 depicted in FIGS. 4-7 are circular, each through hole 312 may include round edges, flat edges, or a non-symmetric shape. FIGS. 11 and 12 show top and isometric views, respectively, of the valve 300 inserted into the hub 210. As shown, the through holes 312 are angularly aligned with posts 260 but are slightly axially offset. In particular, the posts 260 have a centerline diameter that is slightly less than the centerline diameter of the through holes 312. This offset provides improved sealing pressure inward on the valve 300, by ensuring that the valve remains in a stretched state while within the hub. In some embodiments, the posts 260 have a centerline diameter that is the same as the through holes 312 centerline diameter.

The design depicted in FIGS. 11 and 12 ensure that during a peel away action, the valve 300 is stretched, thereby allowing for a smooth break of the hemostasis valve 300 and preventing a double break. This is achieved by angularly spacing the through holes 312 equally except for the spacing between the posts 260 nearest to the notches of the hub 210. In some embodiments the angular spacing is less than or equal to 25 degrees. The ideal angular spacing of through holes 312 for a hemostasis valve 300 with an outer diameter greater than or equal to 15 mm and through hole 312 diameter greater than or equal to 0.75 mm is less than or equal to 25 degrees with spacing between through holes 312 being equal.

FIG. 13 shows a process 1300 for peeling away an introducer 200 having (1) an introducer hub 210 having (a) first and second wings 218a and 218b located opposite each other, and (b) first and second notches 214 located at midpoints between the first and second wings 218a and 218b, (2) a a peel away hemostasis valve 300 within the introducer hub 210, having first and second longitudinal cuts 318a and 318b radially aligned with the first and second notches 214, and (3) an introducer sheath 202 having longitudinal scoring 222 aligned with the first and second notches 214. Process 1300 may be used by a medical health professional after insertion of a medical device through introducer 200. At step 1302, a first force is applied to a first wing 218a of the introducer hub 210 in a first direction radial from the introducer sheath 202 and a second force is applied to the second wing 218b of the introducer hub 210 in a second direction opposite the first direction. For example, the healthcare professional may grasp first and second wings 218a and 218b of the hub 210, and apply a force to the wings 218a and 218b in a direction either toward the elongate sheath 202 or a direction radially extending away from the elongate sheath 202, forcing the first wing 218a toward the second wing 218b depending on the orientations of the first and second wings 218a and 218b relative to the elongate sheath 202.

At step 1304, the first force and the second force are transmitted to the first notch 214 and the second notch of the introducer hub 210, causing the first and second notches 214 to break. For example, the applied force is transmitted from the wings 218a and 218b to a first notch 214 and second notch. The minimum thicknesses at the notches allows the introducer hub 210 to break at the first notch 214 and second notch. Additionally, the shape of the notches concentrate stress to facilitate splitting of the hub 210 along the notches. The minimum thickness and shape of the notches provide a break wall at which a crack may be initiated in the hub 210. In some implementations, the minimum thickness of the notches ranges from 0.075 mm to 0.35 mm.

At step 1306, the hemostasis valve 300 of the introducer hub 210 is broken along the first longitudinal cut 318a and the second longitudinal cut 318b. The first longitudinal cut 318a is aligned with the first notch 214 and the second longitudinal cut 318b is aligned with the second notch For example, a tear starts at the through slits 322a and 322b, located near the edge 306 of the valve and at the radial ends of the longitudinal cuts 318a and 318b, respectively. The tear then propagates radially inward along the portion of the longitudinal cuts 318a and 318b near the second surface 304. This results in the longitudinal cuts 318a and 318b being completely cut through the thickness of the valve. At this point, the valve 300 is still intact at the region between the longitudinal cuts and the helical slits. The tear then proceeds to propagate through this region between the longitudinal cuts 318a and 318b and the helical slits 166. The tear propagation in this region can occur in a radial direction, in a direction through the thickness of the valve 300, or in a vector having components in both directions. The tear propagation in this region results in splitting the peel away hemostasis valve 300 into two pieces along the path described.

At step 1308, the introducer sheath 202 is separated along longitudinal scoring 222 on the introducer sheath 202. The longitudinal scoring 222 is radially aligned with the first notch 214 and the second notch. For example, the longitudinal scoring 222 on the elongate sheath 202 allows the sheath to separate along the length of the elongate sheath 202, and the hub 210 and elongate sheath 202 is peeled away in two pieces. After the introducer is peeled away, the percutaneous pump 100 is left in place in the blood vessel 240.

Other objects, advantages and aspects of the various aspects of the present invention will be apparent to those who are skilled in the field of the invention and are within the scope of the description and the accompanying Figures. For example, but without limitation, structural or functional elements might be rearranged. Similarly, principles according to the present invention could be applied to other examples, which, even if not specifically described here in detail, would nevertheless be within the scope of the present invention.

The invention claimed is:

1. A hemostasis valve body, comprising:
    a first surface and a second surface opposite the first surface;
    an edge extending between an outer perimeter of the first surface and an outer perimeter of the second surface;
    a plurality of helical slits at a center of the hemostasis valve body that traverse the first surface to the second surface, wherein the helical slits provide a seal around a medical device during an insertion of the medical device into a blood vessel; and
    a pair of longitudinal cuts, each longitudinal cut extending from the first surface partially through the hemostasis valve body to a depth short of the second surface for a portion of a length of the respective longitudinal cut or for an entire length of the respective longitudinal cut, wherein the pair of longitudinal cuts facilitates a separation of the hemostasis valve body into two parts during a peel away action, and
    wherein each longitudinal cut is spaced from the helical slits such that an interior edge of each longitudinal cut is at a constant distance from a helical slit closest to the interior edge of the longitudinal cut, and wherein the constant distance is maintained through a thickness of the hemostasis valve body extending from the first surface to the second surface.

2. The hemostasis valve body of claim 1, wherein the pair of longitudinal cuts are angled at an angle of rotation that is same as an angle of rotation of the helical slits.

3. The hemostasis valve body of claim 1, wherein each longitudinal cut is positioned on diametrically opposite sides of the hemostasis valve body.

4. The hemostasis valve body of claim 1, wherein each longitudinal cut traverses the first surface to the second surface for a portion of the length of the respective longitudinal cut or for an entire length of the respective longitudinal cut at the edge.

5. The hemostasis valve body of claim 1, further comprising:
    a first group of lines formed on the first surface, wherein the first group of lines extend radially outward from the center of the hemostasis valve body; and
    a second group of lines formed on the second surface, wherein the second group of lines extend radially outward from the center of the hemostasis valve body.

6. The hemostasis valve body of claim 5, wherein the plurality of helical slits traverse the first group of lines to the second group of lines.

7. The hemostasis valve body of claim 5, wherein the first group of lines are angularly offset from the second group of lines.

8. The hemostasis valve body of claim 1, further comprising a plurality of through holes at a distance from the edge that traverse the first surface to the second surface.

9. The hemostasis valve body of claim 8, wherein each through hole comprises one of round edges, flat edges, and non-symmetric shape.

10. The hemostasis valve body of claim 8, wherein at least some of the plurality of through holes are angularly spaced equally.

11. The hemostasis valve body of claim 10, wherein an angle between adjacent through holes is less than or equal to 25 degrees.

12. The hemostasis valve body of claim 8, wherein the plurality of through holes are sized to accommodate a plurality of posts of an introducer hub.

13. The hemostasis valve body of claim 8, wherein a plurality of posts of an introducer hub are configured to be inserted into the plurality of through holes.

14. The hemostasis valve body of claim 13, wherein the plurality of posts of the introducer hub when inserted into the plurality of through holes keep the hemostasis valve body stretched during a peel away action.

15. The hemostasis valve body of claim 1, wherein the first surface is parallel to the second surface.

16. The hemostasis valve body of claim 1, wherein the first surface and the second surface comprises a planar shape.

17. The hemostasis valve body of claim 1, wherein the first surface comprises one of a conical, tapered, and convex shape.

18. The hemostasis valve body of claim 1, wherein a thickness of the hemostasis valve body is minimum at the center of the hemostasis valve body.

19. The hemostasis valve body of claim 1, wherein the hemostasis valve body comprises one of a disc, cylindrical, and cubic shape.

20. A system for inserting a blood pump into a blood vessel of a patient comprising:
a blood pump; and
an introducer assembly comprising a hub and a sheath, wherein the hub comprises:
   a first wing and a second wing located opposite each other;
   a first notch and a second notch located at mid points between the first wing and the second wing; and
   a hemostasis valve body, wherein the hemostasis valve body comprises:
      a first surface and a second surface opposite the first surface;
      an edge extending between an outer perimeter of the first surface and an outer perimeter of the second surface;
      a plurality of helical slits at a center of the hemostasis valve body that traverse the first surface to the second surface, wherein the helical slits provide a seal around the blood pump during an insertion of the blood pump into a blood vessel;
      a first longitudinal cut; and
      a second longitudinal cut,
      wherein each of the first longitudinal cut and the second longitudinal cut is spaced apart from the helical slits,
      wherein the first longitudinal cut extends from the first surface partially through the hemostasis valve body to a depth short of the second surface for a portion of a length of the first longitudinal cut or for an entire length of the first longitudinal cut,
      wherein the second longitudinal cut extends from the first surface partially through the hemostasis valve body to a depth short of the second surface for a portion of a length of the second longitudinal cut or for an entire length of the second longitudinal cut,
      wherein the first longitudinal cut is radially aligned with the first notch and the second longitudinal cut is radially aligned with the second notch,
      wherein the first longitudinal cut and the second longitudinal cut facilitate a separation of the hemostasis valve body into two parts during a peel away action, and
wherein the hemostasis valve body and the sheath are sized to receive the blood pump.

21. A system for inserting a blood pump into a blood vessel of a patient comprising:
a blood pump; and
an introducer assembly comprising a hub and a sheath, wherein the hub comprises:
   a first wing and a second wing located opposite each other;
   a first notch and a second notch located at mid points between the first wing and the second wing; and
   a hemostasis valve body,
   wherein the hemostasis valve body comprises:
      a first surface and a second surface opposite the first surface;
      an edge extending between an outer perimeter of the first surface and an outer perimeter of the second surface;
      a plurality of helical slits at a center of the hemostasis valve body that traverse the first surface to the second surface, wherein the helical slits provide a seal around the blood pump during an insertion of the blood pump into a blood vessel;
      a first longitudinal cut;
      a second longitudinal cut;
      wherein each of the first longitudinal cut and the second longitudinal cut is spaced apart from the helical slits, wherein the first longitudinal cut extends from the first surface partially through the hemostasis valve body to a depth short of the second surface for a portion of a length of the first longitudinal cut or for an entire length of the first longitudinal cut,
      wherein the second longitudinal cut extends from the first surface partially through the hemostasis valve body to a depth short of the second surface for a portion of a length of the second longitudinal cut or for an entire length of the second longitudinal cut,
      wherein the first longitudinal cut is radially aligned with the first notch and the second longitudinal cut is radially aligned with the second notch,
      wherein the first longitudinal cut and the second longitudinal cut facilitate a separation of the hemostasis valve body into two parts during a peel away action; and
      a plurality of through holes at a distance from the edge that traverse the first surface to the second surface,
wherein the hemostasis valve body and the sheath are sized to receive the blood pump, and
wherein the hub comprises a plurality of posts that are configured to be inserted into the plurality of through holes of the hemostasis valve body during operation of the blood pump.

* * * * *

UNITED STATES PATENT AND TRADEMARK OFFICE
CERTIFICATE OF CORRECTION

PATENT NO. : 11,045,634 B2
APPLICATION NO. : 16/182225
DATED : June 29, 2021
INVENTOR(S) : Christopher Nason Korkuch et al.

It is certified that error appears in the above-identified patent and that said Letters Patent is hereby corrected as shown below:

On the Title Page

Item (56), Column 2, OTHER PUBLICATIONS, Line 1:
Now reads: "Rerport"; should read -- Report --

In the Specification

Column 8, Line 12:
Now reads: "166."; should read -- 316. --

Column 9, Line 3:
Now reads: "a a"; should read -- a --

Column 9, Line 51:
Now reads: "166."; should read -- 316. --

Signed and Sealed this
Twenty-first Day of June, 2022

Katherine Kelly Vidal
*Director of the United States Patent and Trademark Office*